United States Patent [19]

Morgan et al.

[11] Patent Number: 4,988,808

[45] Date of Patent: Jan. 29, 1991

[54] PRODUCTION AND USE OF PORPHYRIN DERIVATIVES AND OF COMPOSITIONS CONTAINING SUCH DERIVATIVES

[75] Inventors: Alan R. Morgan, Swanton; Steven H. Selman, Toledo, both of Ohio

[73] Assignees: The University of Toledo; Medical College of Ohio, Toledo, both of Ohio ; part interest to each

[21] Appl. No.: 448,738

[22] Filed: Dec. 11, 1989

Related U.S. Application Data

[63] Continuation-in-part of Ser. No. 142,034, Jan. 11, 1988, abandoned.

[51] Int. Cl.$^5$ ............................................. C07D 487/22
[52] U.S. Cl. ..................................... 540/145; 534/11; 534/12; 534/13
[58] Field of Search ................... 540/145; 534/11, 12, 534/13

[56] References Cited

U.S. PATENT DOCUMENTS 4,877,872  10/1989  Morgan et al. .................... 540/145
4,883,790  11/1989  Levy et al. .......................... 540/145

FOREIGN PATENT DOCUMENTS 220686  5/1987  European Pat. Off. .
1083185  4/1986  Japan .
857139  8/1981  U.S.S.R. .

Primary Examiner—Richard L. Raymond
Attorney, Agent, or Firm—Willian Brinks Olds Hofer Gilson & Lione

[57] ABSTRACT

A family of benzochlorins, a family of verdins, a family of porphyrin derivatives and metal complexes thereof are disclosed. The benzochlorins have the formula of FIG. 3 of the attached drawings; their metal complexes have the formula of FIG. 1. The verdins have the formula of FIG. 4 of the attached drawings; their metal complexes have the formula of FIG. 2. The porphyrin derivatives have the formula of FIG. 9 of the attached drawings; their metal complexes have the formula of FIG. 10. Solutions of the benzochlorins, verdins, porphyrin derivatives and metal complexes which are physiologically acceptable for intravenous administration are also disclosed, as are emulsions or suspensions of the solutions, and compositions which additionally include cyclodextrin, and wherein the molecules of the benzochlorin, verdin, porphyrin derivatives or metal complex are encapsulated within the molecules of the cyclodextrin. The solvent for the solutions can be a product of the reaction of ethylene oxide with castor oil. A method for detecting and treating tumors in human and animal patients is also disclosed. The method comprises administering one of the benzochlorins, verdins, porphyrin derivatives or metal complexes to the patient. For detection, the tumor area is then illuminated with ultra violet light; for treatment, the tumor area is illuminated with visible light of a wavelength at which the benzochlorin, verdin, porphyrin derivatives or complex administered shows an absorption peak.

2 Claims, 2 Drawing Sheets

PRODUCTION AND USE OF PORPHYRIN DERIVATIVES AND OF COMPOSITIONS CONTAINING SUCH DERIVATIVES

This invention was made with Government support under Grant ROlCA43006 awarded by the National Institutes of Health. The Government has certain rights in the invention.

REFERENCE TO RELATED APPLICATION

This is a continuation in part of application Ser. No. 142,034, filed Jan. 11, 1988 now abandoned.

BACKGROUND OF THE INVENTION

1. Field of the Invention

This invention relates to the production and use of new porphyrin derivatives, to metal complexes of porphyrin derivatives, and to compositions containing the porphyrin derivatives and the metal complexes. More specifically, some of the porphyrin derivatives are compounds for which the name benzochlorins is suggested because they have a chlorin structure with an exocyclic benzene ring fused thereto, metal complexes of the benzochlorins, verdins, metal complexes of verdins, derivatives which form when certain purpurins stand in sunlight in contact with air, and metal complexes of the derivatives which form when the purpurins stand in sunlight in contact with air. All of these compounds are useful in the detection and treatment of tumors; after they have been administered systemically, e.g., intravenously, they localize preferentially in a tumor. After they have been administered, and have localized in a tumor, their presence can be detected by illumination with ultra violet light, which causes them to fluoresce. The porphyrin derivatives of the invention can also be used to treat tumors; after they have been administered and have localized, irradiation with light of a wave length at which they show an absorbance peak causes a reaction which has been found to involve the formation of singlet oxygen, and which damages or destroys the tumor where they have localized. The compositions containing the porphyrin derivatives and metal complexes thereof are solutions in an organic liquid that is physiologically acceptable for intravenous administration, emulsions thereof in saline solutions, or cyclodextrins in whose molecules the molecules of the porphyrin derivatives and metal complexes are encapsulated.

2. The Prior Art

Certain porphyrins and families of purpurins and chlorins and metal complexes thereof and the use of the purpurins, chlorins, metal complexes and porphyrins in the manner described above for the detection and treatment of tumors are all known. For example, PCT/US86/02824 discloses certain purpurins, chlorins, and metal complexes thereof, and their use for the detection and treatment of tumors In addition, European patent application EP142,732 is said (C.A. 103: 123271S) to disclose certain chlorins of a different family and that they accumulate preferentially in the cancer cells of hamsters infected with pancreatic cancer.

Further, a chemical mixture derived from hematoporphyrin, called hematoporphyrin derivative, and often abbreviated "HpD", can be administered intravenously and used in the manner described above for the detection and treatment of tumors. Hematoporphyrin can be produced from protoporphyrin IX, a porphyrin that can be separated from blood. HpD is a mixture of many different porphyrins and related compounds, the exact composition not being fully known (see, for example, *Porphyrin Photosensitization,* edited by David Kassel and Thomas J. Dougherty, Plenum Press, New York and London, 1983, pp. 3-13). As a consequence, the chlorins and purpurins of PCT/US86/02824 are preferred over HpD for this use because they are single, known compounds. In addition, the chlorins and purpurins have absorbance peaks at longer wavelengths and show greater absorbances, by comparison with HpD; the longer wavelength peaks are advantageous because light of the longer wavelengths is capable of greater penetration of tissue, while the greater absorbances are desirable because less light energy is required to cause a given degree of reaction.

The production of the nickel complex of an octaethyl benzochlorin has been disclosed (Arnold et al., *J.C.S. PERKIN I,* pages 1660-1670, 1979). The complex is produced by reaction in dry NN-dimethylformamide between phosphorus oxychloride and nickel meso-vinyl octaethylporphyrin. The major product reported was nickel 5-($\beta$-Formylvinyl) octaethylporphyrin (80 percent yield); in addition, the authors reported a 5 percent yield of the nickel benzochlorin and a 15 percent yield of a demetallated product (which was not a benzochlorin) The nickel octaethylbenzochlorin has been found to be substantially inert insofar as the ability to cause a cytotoxic response is concerned.

The production of a verdin isomer mixture by refluxing a mesorhodin isomer mixture in acetic acid has been reported (*The Porphyrins, Volume II,* pages 137 and 138, edited by David Dolphin, Academic Press, New York, San Francisco and London, 1978. Woodward et al. J.A.C.S., 1960, 82, p. 3800 and Morgan, J.Org.Chem., 1986, 51, 1347 disclose that the porphyrin derivatives form when purpurins stand in sunlight in the presence of air.

The benzochlorins, the verdins, the derivatives which form when purpurins stand in sunlight in contact with air and metal complexes of the instant invention have the same advantages as the purpurins, chlorins and metal complexes, and, in some cases, the significant additional advantage that substantially smaller doses are required to cause a given cytotoxic response.

BRIEF DESCRIPTION OF THE INVENTION

Figure 1:
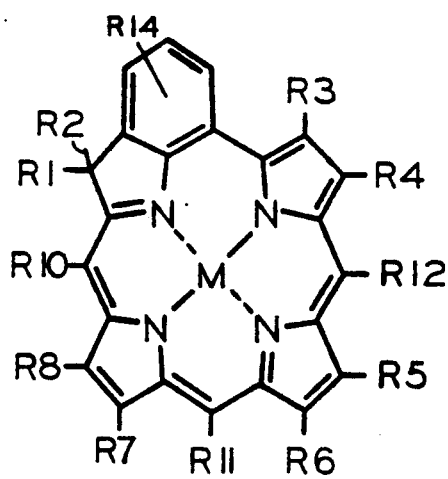
FIG. 1 is a structural formula for metal complexes of the family of benzochlorins according to the invention.
Figure 2:
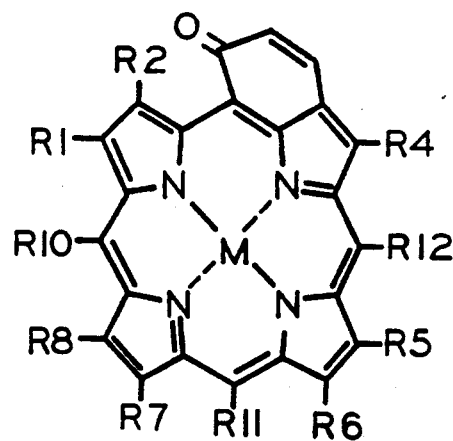
FIG. 2 is a structural formula for metal complexes of a family of verdins according to the invention.
Figure 3:
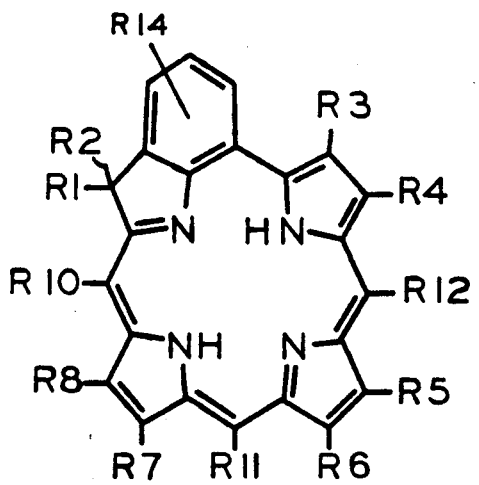
FIG. 3 is a structural formula for the family of benzochlorins according to the invention.
Figure 5:
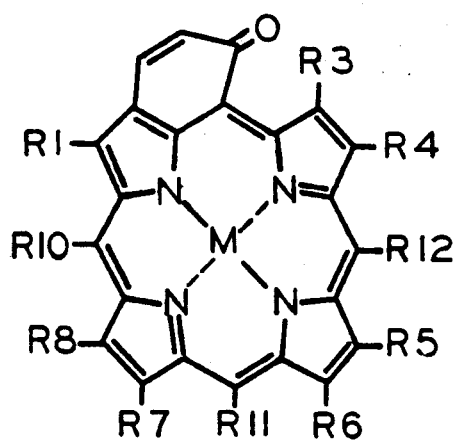
FIG. 5 is a structural formula for metal complexes of a family of verdins which may be isomers of the complexes of FIG. 2.
Figure 10:
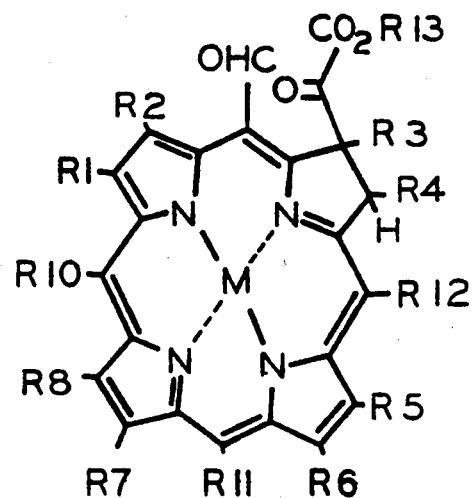
FIG. 10 is a structural formula for metal complexes of the porphyrin derivatives of FIG. 9.

The instant invention, in one aspect, is a metal complex of a benzochlorin, of a verdin, or of a porphyrin derivative having the structure of FIG. 1, of FIG. 2, of FIG. 5 or of FIG. 10 or is a benzochlorin having the structure of FIG. 3 of the attached drawings, where M is a metal, for example, Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh, Sb, Sc, Sm, Sn, Tb, Th, Ti, Tl, Tm, U, V, Y, Yb, Zn or Zr, $R13$ is an alkyl group having from 1 to 4 carbons, and each of $R1$ through $R12$ and $R14$ is:

H or CHO, a primary or secondary alkyl group having from 1 to 4 carbon atoms, an alkylene group having from 2 to 4 carbon atoms, a group having the formula $R_2N(R_3)_2$ where $R_2$ is a bivalent aliphatic hydrocarbon radical having from 1 to 4 carbon atoms, wherein any carbon to carbon bond is either a single or a double bond, and not more than one is a double bond; $R_3$ is hydrogen or an alkyl radical having from 1 to 2 carbon atoms and the two $R_3$ groups can be the same or different, a group having the formula $R_2N(R_4)_3^+$ where $R_2$ is a bivalent aliphatic hydrocarbon radical having from 1 to 4 carbon atoms, wherein any carbon to carbon bond is either a single or a double bond, and not more than one is a double bond; and $R_4$ is an alkyl group having from 1 to 2 carbon atoms and the three $R_4$ groups can be the same or different, a group having the formula $R_2OH$ were $R_2$ is a bivalent aliphatic hydrocarbon radical having from 1 to 4 carbon atoms, wherein any carbon to carbon bond is either a single or a double bond, and not more than one is a double bond, or $CO_2R'$, $CH_2CO_2R'$ or $CH_2CH_2CO_2R'$ where $R'$ is H, or a primary or secondary alkyl group having from one to four carbon atoms, with the proviso that $R14$ can be $SO_3H$ or a physiologically acceptable salt thereof.

In another aspect, the invention is a solution in an organic liquid which is physiologically acceptable for intravenous or topical administration of one of the foregoing benzochlorins, verdins, porphyrin derivatives or metal complexes, or an aqueous emulsion of such a solution.

In still another aspect, the invention is a structure in which the molecules of one of the foregoing benzochlorins, verdins, porphyrin derivatives or metal complexes are encapsulated in the molecules of a cyclodextrin.

In yet another aspect, the invention is a method for detecting and treating tumors which comprises administering an effective amount of one of the foregoing benzochlorins, a metal complex of one of the foregoing benzochlorins, one of the foregoing verdins, a metal complex of one of the foregoing verdins, one of the foregoing porphyrin derivatives, or a metal complex of one of the foregoing porphyrin derivatives to a human or animal patient, and irradiating the relevant region of the patient with ultra violet or visible light of a wavelength at which the benzochlorin, benzochlorin metal complex, verdin, verdin metal complex, porphyrin derivative or porphyrin derivative metal complex has an absorbance peak.

OBJECTS OF THE INVENTION

It is, therefore, an object of the invention to provide a new composition which is a benzochlorin having the structure of FIG. 3 of the attached drawings, a metal complex of a benzochlorin having the structure of FIG. 1 of the attached drawings, a metal complex of a verdin having the structure of FIG. 2 or of FIG. 5 of the attached drawings, or a metal complex of a porphyrin derivative having the structure of FIG. 10 of the attached drawings.

Figure 4:
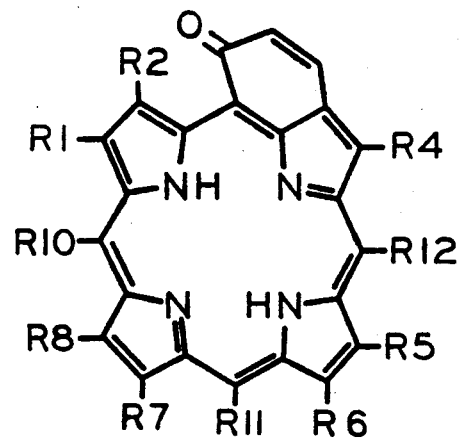
FIG. 4 is a structural formula for verdins of the family of FIG. 2.
Figure 6:
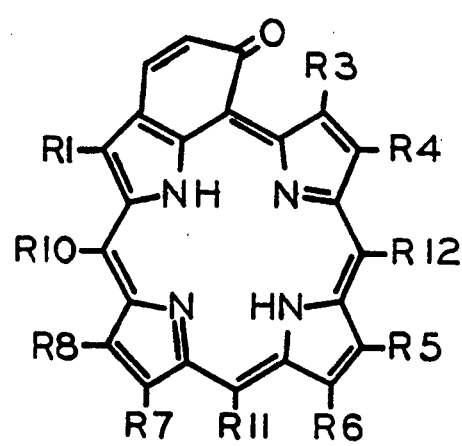
FIG. 6 is a structural formula for verdins of the family of FIG. 5.
Figure 9:
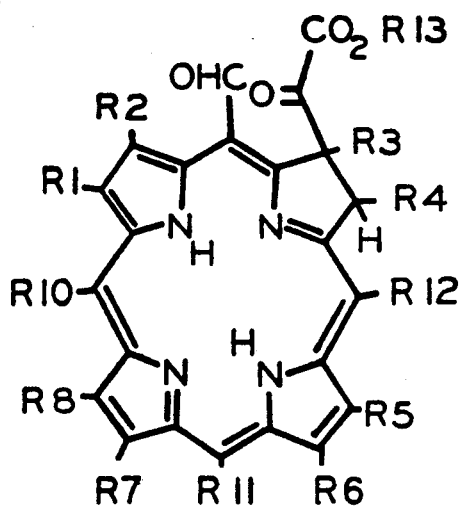
FIG. 9 is a structural formula for a family of porphyrin derivatives which form when the corresponding purpurins stand in sunlight in the presence of air.

It is another object of the invention to provide a solution in an organic liquid of a benzochlorin having the structure of FIG. 3 of the attached drawings, a metal complex of a benzochlorin having the structure of FIG. 1 of the attached drawings, a verdin having the structure of FIG. 4 or FIG. 6 of the attached drawings, a metal complex of a verdin having the structure of FIG. 2 or FIG. 5 of the attached drawings, a porphyrin derivative having the structure of FIG. 9 of the attached drawings, or a metal complex of a porphyrin derivative having the structure of FIG. 10 of the attached drawings.

It is a further object to provide an aqueous emulsion of a solution in an organic liquid of a benzochlorin having the structure of FIG. 3 of the attached drawings, a metal complex of a benzochlorin having the structure of FIG. 1 of the attached drawings, a verdin having the structure of FIG. 4 or FIG. 6 of the attached drawings, a metal complex of a verdin having the structure of FIG. 2 or FIG. 5 of the attached drawings, a porphyrin derivative having the structure of FIG. 9 of the attached drawings, or a metal complex of a porphyrin derivative having the structure of FIG. 10 of the attached drawings.

It is still another object of the invention to provide a composition in which molecules of a benzochlorin having the structure of FIG. 3 of the attached drawings, a metal complex of a benzochlorin having the structure of FIG. 1 of the attached drawings, a verdin having the structure of FIG. 4 or of FIG. 6 of the attached drawings, a metal complex of a verdin having the structure of FIG. 2 or of FIG. 5 of the attached drawings, a porphyrin derivative having the structure of FIG. 9 of the attached drawings, or a metal complex of a porphyrin derivative having the structure of FIG. 10 of the attached drawings are encapsulated in the molecules of a cyclodextrin.

It is yet another object of the invention to provide a method for detecting and treating tumors which comprises administering one of the foregoing benzochlorins, benzochlorin metal complexes, verdins, verdin metal complexes, porphyrin derivatives or porphyrin derivative metal complexes to a human or animal patient.

DESCRIPTION OF THE PREFERRED EMBODIMENTS

Examples 1 through 9 hereof set forth the best mode presently contemplated by the inventors, insofar as this invention is directed to benzochlorins, benzochlorin metal complexes, verdins, verdin metal complexes, porphyrin derivatives and porphyrin derivative metal complexes and their production. The in vivo test procedures describe the best mode insofar as this invention is directed to solutions of the benzochlorins, benzochlorin metal complexes, verdins, verdin metal complexes, porphyrin derivatives and porphyrin derivative metal complexes in an organic liquid and to the production of such solutions, and the in vivo test procedures describe the best mode insofar as the invention is directed to the use of benzochlorins, benzochlorin metal complexes, verdins, verdin metal complexes, porphyrin derivatives and porphyrin derivative metal complexes for the detection and treatment of tumors.

In the examples, and elsewhere herein, the term "percent $v/v$" means percent by volume; the term "percent $w/w$" means percent by weight; the term "alkyl group" is used in its ordinary sense to mean a monovalent, saturated, aliphatic hydrocarbon radical; the term "alkylene group" is used in its ordinary sense to mean a monovalent, aliphatic hydrocarbon radical which has one carbon to carbon double bond and in which any other carbon to carbon bond is a single bond; all temperatures are in °C.; and the following abbreviations have the meanings indicated: mg=milligram or milligrams; g=gram or grams; kg=kilogram or kilograms; ml=milliliter or milliliters; cm=centimeter or centimeters; $\epsilon$=molar absorptivity; mw=milliwatts; and nm=nanometer or nanometers.

EXAMPLE 1

Figure 8:
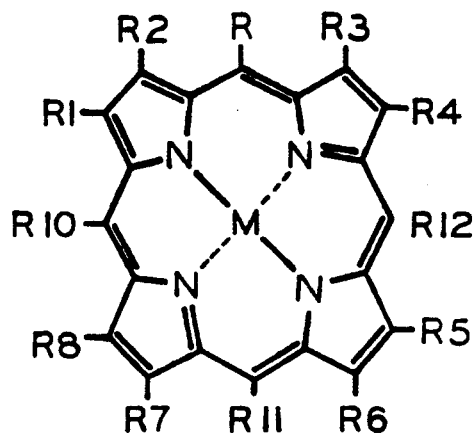
FIG. 8 is a structural formula for metal complexes of porphyrins which can be used to produce benzochlorins and metal complexes thereof according to the invention.

The production of a novel benzochlorin according to the invention (hereafter "octaethyl benzochlorin") from nickel meso-formyl octaethyl porphyrin is described in this example. The production of nickel meso-formyl octaethyl porphyrin is described in a journal article by R. Grigg et al., J. Chem. Soc. Perkin Trans I, 1972, pp. 1789,1798; it has the formula of FIG. 8 of the attached drawings where R1 through R8 are ethyl, R10 through R12 are hydrogen, R is CHO, and M is Ni. Four intermediates were produced in the Example 1 procedure, nickel meso-($\beta$-ethoxycarbonylvinyl)- octaethyl porphyrin, which has the formula of FIG. 8 of the attached drawings where R1 through R8 are ethyl, R10 through R12 are hydrogen, R is CH=CHCO$_2$CH$_2$CH$_3$, and M is Ni, nickel meso($\beta$-hydroxymethyl- vinyl) octaethyl porphyrin, which has the formula of FIG. 8 of the attached drawings where R1 through R8 are ethyl, R10 through R12 are hydrogen, R is CH=CHCH$_2$OH, and M is nickel, nickel meso-($\beta$-formylvinyl)octaethyl porphyrin, which has the formula of FIG. 8 of the attached drawings where R1 through R8 are ethyl, R10 through R12 are hydrogen, R is CH=CHCHO, and M is nickel, and nickel octaethyl benzochlorin, which has the formula of FIG. 1 of the attached drawings where R1 through R8 are ethyl, R10 through R12 are hydrogen, and M is nickel. Octaethyl benzochlorin has the formula of FIG. 3 of the attached drawings where R1 through R8 are ethyl, and R10 through R12 are hydrogen.

Production of nickel meso-($\beta$-ethoxycarbonylvinyl)octaethyl porphyrin

A solution of 506 mg nickel meso-formyl octaethyl porphyrin and 1.024 g (carbethoxymethylene)triphenylphosphorane in 50 ml xylene was heated under reflux for 18 hours. The solution was cooled; the xylene was removed in vacuo; and the solid which remained was dissolved in the minimum amount of dichloromethane and chromatographed on silica. A minor fraction of nickel octaethyl porphyrin and a major red fraction were recovered. The solvent was removed from the red fraction; the solid which remained was recrystallized from a solvent composed of equal parts by volume of dichloromethane and methanol, yielding 455 mg small brown needles. The product was identified by nuclear magnetic resonance as nickel meso-($\beta$-ethoxycarbonylvinyl) octaethyl porphyrin; it showed visible spectrum absorbance peaks at 405, 530 and 565 nanometers (94 180, 18 604, 27 790).

Production of nickel meso-($\beta$-hydroxymethylvinyl)octaethyl porphyrin

Two solutions were prepared, a first by dissolving 50 mg nickel meso-($\beta$-ethoxycarbonylvinyl)octaethyl porphyrin in 50 ml dry diethyl ether under nitrogen and a second by dissolving 5 mg lithium aluminum hydride in 10 ml diethyl ether. The first solution was kept under nitrogen while the second was added quickly thereto at room temperature of about 22°, and the solution which resulted was allowed to stand for 24 hours under nitrogen. The reaction was then quenched by making incremental additions of 15 percent $w/w$ aqueous ammonium chloride until an addition did not cause effervescence. The organic layer was then collected and washed with three 50 ml portions of water. The solvent was then evaporated, and the solid residue was chromatographed on silica gel, using dichloromethane as the solvent. The major red band was collected. Red crystals of the desired product were recovered by evaporating the solvent and were crystallized from dichloromethane containing 2 percent $v/v$ methanol. The yield was 26 percent of theory, U V lambda maximum 559 nm.

Production of Nickel meso-($\beta$-formylvinyl)octaethyl porphyrin

A solution was prepared by dissolving 100 mg nickel meso-($\beta$-hydroxymethylvinyl)octaethyl porphyrin and 108 mg pyridine dichromate in 100 ml dichloromethane, and was allowed to stand under a nitrogen atmosphere for about 16 hours. The dichloromethane was then evaporated and the reaction products were dissolved in diethyl ether, leaving a residue of insoluble chromium salts, which were separated by filtration. The organic layer was collected. The diethyl ether was removed by evaporation and the product was chromatographed on a silica gel column, using dichloromethane as the eluent. The major reddish green fraction was collected; the solvent was removed by evaporation and the residue was crystallized from dichloromethane containing 2 percent $v/v$ methanol. The crystallized product was identical, spectroscopically, to that reported in the literature (Arnold et al., *J.C.S. PERKIN I*, pages 1660–1670, 1979).

Production of Ni Octaethyl benzochlorin

A 200 mg portion of Ni meso-($\beta$-formylvinyl) octaethyl porphyrin was treated with 4 ml concentrated (98 percent $w/w$) sulfuric acid for two hours. The reaction product was then poured into 20 ml water, neutralized with sodium hydrogen carbonate, and extracted with dichloromethane. The organic layer was collected and washed with water, and the dichloromethane was removed by evaporation. The residue was chromatographed on silica gel, using dichloromethane as the solvent. The major green band was collected, and the solvent was removed by evaporation. The residue was crystallized from dichloromethane containing 2 percent $v/v$ methanol. The crystallized product (yield, 40 percent) was identical, spectroscopically, to that reported in the literature (Arnold et al., *J.C.S. PERKIN I*, pages 1660–1670, 1979).

Production of Octaethyl benzochlorin

A 40 mg portion of nickel octaethyl benzochlorin was stirred for 2¼ hours in 4 ml concentrated (98 percent w/w) sulfuric acid. The reaction mixture which resulted was poured onto ice, neutralized with sodium hydrogen carbonate, and extracted with dichloromethane. Two reaction products (20 mg of each) were recovered by chromatographing the extract on silica gel. One of the products was identified as octaethyl benzochlorin, while the other was identified as the sulfonate thereof. The sulfonate was found to have the structure of FIG. 3 of the drawings, where R13 is $SO_3Na$, and is attached either to the available carbon nearer R2 or to the available carbon nearer R3, probably the former. The octaethyl benzochlorin was crystallized from dichloromethane containing 2 percent v/v methanol, while the octaethyl benzochlorin sulfonate was crystallized from dichloromethane. Lambda maximum, U V, was 657 nm for both products. The $SO_3Na$ group can be converted to $SO_3H$ by acidifying the sulfonate, and the hydrogen of the $SO_3H$ group can be converted to other cations by neutralizing with other bases.

EXAMPLE 2

Production of Zn Octaethyl Benzochlorin

A solution was prepared by dissolving 20 mg octaethyl benzochlorin in a mixed solvent composed of 15 ml dichloromethane and 5 ml methanol and 100 mg zinc acetate was added to the solution; the mixture which resulted was refluxed for about 24 hours until the electronic spectrum of the reaction mixture indicated that chelation was complete. The reaction mixture was then concentrated to 7 ml and allowed to cool to room temperature of about 22°. Product which precipitated was recovered by filtration, dissolved in a mixed solvent composed of 5 ml dichloromethane and 2 ml methanol, and recrystallized, yielding 18 mg Zn octaethyl benzochlorin in the form of microcrystals. The Zn octaethyl benzochlorin, a metal complex, has the formula of FIG. 1 of the attached drawings where R1 through R8 are ethyl, R10 through R12 are hydrogen and M is Zn; the compound has a visible spectrum absorbance peak at 850 nanometers.

EXAMPLE 3

The production of "Verdin I" from coproporphyrin I, tetramethyl ester, is described in this Example. The coproporphyrin I, tetramethyl ester, starting material had the structure of FIG. 7 of the attached drawings where R and R10 through R12 are hydrogen, R1, R3, R5, and R7 are $CH_3$ and R2, R4, R6 and R8 are $CH_2CH_2CO_2CH_3$. "Verdin I" has the structure of FIG. 6 of the attached drawings where R10 through R12 are hydrogen, R1, R3, R5, and R7 are $CH_3$ and R4, R6, and R8 are $CH_2CH_2COOCH_3$.

Production of Verdin I

A 100 mg portion of coproporphyrin I, tetramethyl ester was heated to 80° with 2 ml concentrated (98 percent w/w) sulfuric acid for about 5 hours until an absorbance peak developed in the visible spectrum at 695 nm. The reaction product was then cooled and stirred for 16 hours in 100 ml methanol. Solvent was then removed from the solution by evaporation until its volume was 20 ml, and the concentrated solution was poured into an equal volume of water. Organic material was then extracted into dichloromethane and solvent was removed from the extract by evaporation. The solid residue was chromatographed on silica gel, using dichloromethane containing 2 percent v/v of methanol as the eluent. A major green band was collected, and the Verdin I was recovered by evaporating the solvent. It was found to have an absorbance peak in the visible spectrum at 695 nm. The Verdin I zinc complex was prepared by the method described in Example 2; it was found to have a very broad absorbance peak in the visible spectrum spanning 680 to 725 nm.

EXAMPLE 4

The procedure described in Example 1 has been used to produce other benzochlorins. A typical one of the starting materials, Nickel meso-formyletio porphyrin I, produced four intermediates [I] Nickel meso-(β-ethoxycarbonylvinyl)-etio porphyrin I, [II] Nickel meso-(β-hydroxymethylvinyl)- etio porphyrin I, [III] Nickel meso-(β-formylvinyl)-etio porphyrin I and [IV] Nickel etiobenzochlorin. Both etiobenzochlorin and its sodium sulfonate (structure of FIG. 3 where R14 is $SO_3Na$) were produced. The starting material and all of the first three intermediates have the structure of FIG. 8 of the attached drawings where R1, R3, R5, and R7 are $CH_3$, R2, R4, R6 and R8 are $CH_2CH_3$, R10 through R12 are hydrogen, and M is nickel. R is CHO in the starting material, $CH=CHCO_2CH_2CH_3$ in the first intermediate, $CH=CHCH_2OH$ in the second intermediate, and $CH=CHCHO$ in the third intermediate. The fourth intermediate was a mixture of two isomers, one having the structure of FIG. 1, and one having a similar structure, except that it was the pyrrole ring to which R3 and R4 were attached that was reduced, and to which the benzene ring was fused. The etiobenzo chlorin was also a mixture of two isomers, one having the structure of FIG. 3, and one having a similar structure, except that it was the pyrrole ring to which R3 and R4 were attached that was reduced, and to which the benzene ring was fused.

The procedure of Example 3 has been used to produce other verdins. Typical ones of the starting materials and of the verdins produced are set forth in Examples 5 through 7.

EXAMPLE 5

Figure 7:
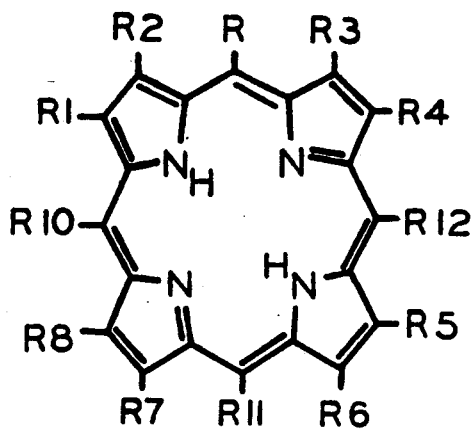
FIG. 7 is a structural formula for a family of porphyrins which can be used to produce verdins and metal complexes thereof according to the invention.

| Compound | Formula of |
| --- | --- |
| Starting Material, Deuteroporphyrin IX | FIG. 7* |
| Final product, an isomeric mixture of Verdin II | FIG. 4* |
| and Verdin III | FIG. 6 |

*where:
R1, R4, R6 and R8 are $CH_3$, and R5, R7 and R10 through R12 are hydrogen;
In the starting material, R is hydrogen and R2 and R3 are $CH_2CH_2COOCH_3$;
In Verdin II, R2 is $CH_2CH_2COOCH_3$;
In Verdin III, R3 is $CH_2CH_2COOCH_3$.

EXAMPLE 6

| Compound | Formula of |
| --- | --- |
| Starting Material, Meso-porphyrin IX | FIG. 7* |
| Final product an isomeric mixture of Verdin IV | FIG. 4* |
| and Verdin V | FIG. 6* |

*Where:
R1, R4, R6 and R8 are $CH_3$, R5 and R7 are $CH_2CH_3$, and R10 through R12 are hydrogen.
In the starting material, R is hydrogen and R2 and R3 are $CH_2CH_2COOCH_3$.
In Verdin IV, R2 is $CH_2CH_2COOCH_3$.
In Verdin V, R3 is $CH_2CH_2COOCH_3$.

EXAMPLE 7

| Compound | Formula of |
| --- | --- |
| Starting Material, Methyl pyrroporphyrin | FIG. 7* |
| Final product, Verdin VI | FIG. 6* |

*Where:
R1, R3, R6 R7 and R8 are $CH_3$, R4 and R5 are $CH_2CH_3$ and R10 through R12 are hydrogen.
In the starting material, R2 is $CH_2CH_2COOCH_3$ and R is hydrogen.

The procedure was modified, by comparison with that of Example 3, in that, after the visible spectrum peak developed at 695 nm, the steps of pouring the reaction product into 100 ml methanol and stirring for 16 hours were omitted. The purpose of these steps, in Example 3, was to re-esterify any free COOH groups; they were unnecessary in Example 7, because neither the starting porphyrin nor Verdin VI includes a moiety that would form free COOH groups.

The production of a porphyrin derivative having the structure of FIG. 9 of the attached drawings from the corresponding purpurin is described in the following example.

EXAMPLE 8

A 50 mg portion of Purpurin NT2 was dissolved in 20 ml dichloromethane, and the resulting solution was allowed to stand for a total of 16 hours in sunlight, in contact with air, and under ambient conditions (temperature about 22°). The dichloromethane was then removed by evaporation, leaving 50 mg porphyrin derivative (hereafter "Porphyrin NT2") which was found by nuclear magnetic resonance to have the formula of FIG. 9 of the attached drawings where R1 through R8 are ethyl, R10 through R12 are hydrogen, and R13 is $CH_2CH_3$. The production of Purpurin NT2 is described in Example 1 of PCT/US86/02824; it has the formula of FIG. 5 of the drawings of that application where R1 through R8 are ethyl, R9 is $CO_2CH_2CH_3$, and R10 through R13 are hydrogen.

The production of a porphyrin derivative metal complex having the structure of FIG. 10 of the attached drawings from the corresponding purpurin metal complex is described in the following example.

EXAMPLE 9

A 50 mg portion of Zn Purpurin NT2 was dissolved in 20 ml dichloromethane, and the resulting solution was allowed to stand for a total of 16 hours in sunlight, in contact with air, and under ambient conditions (temperature about 22°). The dichloromethane was then removed by evaporation, leaving 50 mg porphyrin derivative, zinc complex (hereafter "Zn Porphyrin NT2") which was found by nuclear magnetic resonance to have the formula of FIG. 10 of the attached drawings where R1 through R8 are ethyl, R10 through R12 are hydrogen, and R13 is $CH_2CH_3$. The production of Zn Purpurin NT2 is described in Example 2 of PCT/US86/02824; it has the formula of FIG. 1 of the drawings of that application where R1 through R8 are ethyl, R9 is $CO_2CH_2CH_3$, R10 through R13 are hydrogen, and M is Zn.

The procedures of Examples 8 and 9 have been used to produce other porphyrin derivatives and metal complexes from purpurins and purpurin metal complexes disclosed in PCT/US86/02824 Examples of the porphyrin derivatives and metal complexes are given in the following table, where names are assigned to the porphyrin derivatives and metal complexes. In all cases, names used in the table for the purpurins and purpurin metal complexes have the meanings set forth therefor in the PCT application, and the structural differences between the porphyrin derivatives and metal complexes and the purpurins and purpurin metal complexes from which they are produced are analogous to those between Porphyrin NT2 and Purpurin NT2.

| Purpurin or Metal Complex | Porphyrin derivative or Metal Complex |
| --- | --- |
| Sn(IV) Purpurin NT2 | Sn(IV) Porphyrin NT2 |
| Purpurin ET2 | Porphyrin ET2 |
| Zn Purpurin ET2 | Zn Porphyrin ET2 |
| Sn(IV) Purpurin ET2 | Sn(IV) Porphyrin ET2 |

In vivo testing of various compounds according to the invention was conducted on male Fisher 344 rats weighing 135 to 150 g in whom the transplantable FANFT (N-[4-(5-nitro2-furyl)-2-thiazolyl]formamide tumor system had been implanted. (Use of this system is reported by Selman, S. H., et al., Cancer Research, pp. 1924-1927, May, 1984.) Two tumors were implanted into the subcutaneous tissue of the flanks of each test animal; when the testing was carried out, each tumor was about 1 cm in diameter.

In some instances, the compounds tested were dissolved in a commercially available non-ionic solubilizer and emulsifier obtained by reacting ethylene oxide with castor oil in a ratio of 35 moles of ethylene oxide per mole of castor oil, diluting the resulting solution with 1,2-propanediol, and producing an emulsion with the resulting solution and 0.9 percent w/w aqueous sodium chloride solution. The specific non-ionic solubilizer used is available from BASF under the designation CREMOPHOR EL; it is composed of fatty acid esters of polyglycols, glycerol polyglycols, polyethylene glycols and ethoxylated glycerol. The test solutions were prepared from 5 mg test compound, 0.5 ml warm solubilizer (enough to dissolve the test compound), enough 1,2-propanediol to make a solution of the test compound in a mixed diol/solubilizer solvent containing 32.9 percent w/w solubilizer; finally, enough 0.9 percent w/w aqueous sodium chloride was added to make 2 ml test solution so that the final concentration of the test compound in the test solution was 2.5 mg per ml. Each test solution was made, with mechanical shaking and stirring, by dissolving the test compound in the solubilizer, diluting the resulting solution with the indicated amount of 1,2-propanediol, and adding the sodium chloride solution to the diluted solution. A control solution was also prepared for use with each test solution. The control was identical with the test solution except that it contained no test compound. The test solutions were prepared in air, but it is believed that a nitrogen atmosphere would be advantageous because it would minimize the chance of a reaction with oxygen.

In other cases a solution made by dissolving 5.2 $\mu$mole of the compound under test in 1 ml chloroform was mixed with a 0.1M phosphate buffer containing 150 $\mu$mole sodium chloride and 20.8 $\mu$mole $\tau$-cyclodextrin, and the resulting composition was vortexed under pressure until the chloroform had evaporated completely, at which time it was found that an aqueous solution of an inclusion complex had been produced in which the molecules the compound under test were encapsulated within molecules of the cyclodextrin.

Molecules of phthalocyanines, for example, zinc phthalocyanine, can also be encapsulated within cyclodextrin molecules by the method described in the preceding paragraph, but a different solvent, e.g., tetrahydrofuran, should be substituted for the chloroform. Such compositions are significantly advantageous by comparison with previously known delivery systems for phthalocyanines.

Three cyclodextrins are known, $\alpha$, $\beta$ and $\tau$. The molecules of all three are annular rings 0.78 nm high. The outer and inner diameters are, for $\beta$-cyclodextrin, 1.37 and 0.57 nm, for $\beta$-cyclodextrin, 1.53 and 0.78 nm, and, for $\tau$-cyclodextrin, 1.69 35 and 9.5 nm.

The testing involved injecting each rat with a solution of the compound under test, dosage 1 mg test compound per kg of body weight or with the same volume of the appropriate control, irradiating one of the two tumors with light for 30 minutes, sacrificing the animals, and examining the tumors. The injections were made via the dorsal tail vein. The irradiation of one of the tumors occurred twenty four hours after each rat was injected while the other of the two tumors was shielded by an opaque box.

Tumor temperature and body core temperature were monitored, using thermistors, one placed into the tumor and one placed intrarectally. Tumor temperature was kept within 2° of body core temperature by directing a jet of cool air over the tumor.

The light source was a slide projector that had a 500 watt bulb fitted with a red filter which is available from Corning Glass Works under the designation 2418. The light was reflected 90° by a silvered mirror, and was focused onto the tumor with a secondary condensing lens. The light intensity on the tumor was monitored, using a photometer/radiometer that is available from United Detector Technology under the designation "UDT #351", and was maintained at 200 mw per $cm^2$.

Six rats were injected with each test solution and two were injected with the appropriate control solution Four hours after the irradiation, three of the rats that had been injected with the test solution and one of the rats that had been injected with the control were sacrificed by an intracardiac injection of saturated aqueous potassium chloride solution. Twenty four hours after the irradiation, another three of the rats that had been injected with the test solution and the other rat that had been injected with the control were sacrificed in the same way. During the testing, the rats were under barbituate anesthesia (65 mg per kg body weight).

The tumors were then excised, placed in 10 percent w/w phosphate-buffered formalin and cut into three sections perpendicular to their long axis. The tumors were then embedded in paraffin and cut into sections five microns in width. The sections were stained with hematoxylin and eosin.

Histologic examination of the stained sections revealed that all purpurins, benzochlorins, porphyrin derivatives (FIG. 9 of the attached drawings) and verdins tested, and their metal complexes, with the exception of the nickel complexes, produced hemorrhage, vacuolization, vascular stasis and necrosis. The purpurins and benzochlorins were the most active compounds, followed by the porphyrin derivatives (FIG. 9) and the verdins. This test did not show a difference between emulsions of the compounds and cyclodextrin solutions in which molecules of the compounds were encapsulated within molecules of the cyclodextrin.

The production of Octaethyl benzochlorin, Zn octaethyl benzochlorin, Verdin I, Verdin I zinc complex, Etiobenzochlorin, an isomeric mixture of Verdin II and Verdin III, an isomeric mixture of Verdin IV and Verdin V, Verdin VI, Porphyrin NT2, and Zn Porphyrin NT2 is described in the foregoing Examples hereof. In each case, the benzochlorin had the structure of FIG. 3 of the attached drawings and the verdin the structure of FIG. 4 where R1 through R8 had certain meanings and R10 through R12 were hydrogen. The benzochlorins were produced from metal complexes of porphyrins having the structure of FIG. 8 of the attached drawings where R1 through R8 meant the same as in the benzochlorins, R was CHO, and R10 through R12 were hydrogen. The verdins were produced from porphyrins having the structure of FIG. 7 of the attached drawings where one of R2, R3, R6 and R7 had the structure $CH_2CH_2COOR'$, where R' is an alkyl group, preferably methyl, and the others of R1 through R8 had the same meanings as in the verdins.

The other metal porphyrins which are required for substitution in the procedure of Example 1 for nickel meso-formyl octaethyl porphyrin to produce the benzochlorins having the structure of FIG. 3 of the drawings where R10 through R12 are hydrogen are either disclosed in the literature or can be produced by methods that are disclosed in the literature. Similarly, the other porphyrins which are required for substitution in the procedure of Example 3 for coproporphyrin I, tetramethyl ester to produce the verdins having the structure of FIG. 4 of the drawings where R10 through R12 are hydrogen are either disclosed in the literature or can be produced by methods that are disclosed in the literature.

In general, porphyrins are produced by condensing two pyrroles, and by then condensing two of the condensation products. The two condensation products can be the same or different, and each can be made by condensing two pyrroles that are the same or different. The pyrroles necessary to produce porphyrins having the structure of FIG. 7 of the attached drawings where R is H or CHO, R10 through R12 are hydrogen, and each of R1 through R8 is H or CHO, a primary or secondary alkyl group having from 1 to 4 carbon atoms, an alkylene group having from 2 to 4 carbon atoms, a group having the formula $R_2N(R_3)_2$ where $R_2$ is a bivalent aliphatic hydrocarbon radical having from 1 to 4 carbon atoms, wherein any carbon to carbon bond is either a single or a double bond, and not more than one is a double bond; $R_3$ is hydrogen or an alkyl radical having from 1 to 2 carbon atoms and the two $R_3$ groups can be the same or different, a group having the formula $R_2N(R_4)_3^+$ where $R_2$ is a bivalent aliphatic hydrocarbon radical having from 1 to 4 carbon atoms, wherein any carbon to carbon bond is either a single or a double bond, and not more than one is a double bond; and $R_4$ is an alkyl group having from 1 to 2 carbon atoms and the three $R_4$ groups can be the same or different, a group having the formula $R_2OH$ were $R_2$ is a bivalent aliphatic hydrocarbon radical having from 1 to 4 carbon atoms, wherein any carbon to carbon bond is either a single or a double bond, and not more than one is a double bond, or $CO_2R'$, $CH_2CO_2R'$ or $CH_2CH_2CO_2R'$ where R' is H, or a primary or secondary alkyl group having from one to four carbon atoms, are all known or can be made by known methods. The nickel complex can be made by the method disclosed in Example 2, substituting the porphyrin for the benzochlorin and nickel acetate for zinc acetate. To produce benzochlorins, the alkoxycarbonylvinyl group, the β-hydroxyalkylvinyl group and the β-formylvinyl can then be introduced in the known way disclosed in Example 1 hereof. To produce verdins, a porphyrin starting material wherein at least one of R2, R3, R6 and R7 is $CH_2CH_2COOR'$ is subjected to the procedure of Example 3. These porphyrins produce, (a) when used in the procedure of Example 1, benzochlorins having the structure of FIG. 3 of the attached drawings where R10 through R12 and R14 are hydrogen, and, (b) when used in the procedure of Example 3, verdins having the structure of FIG. 4 of the attached drawings where R10 through R12 are hydrogen Such benzochlorins and verdins can be reacted with the Vilsmier reagent to introduce a formyl group, as R10 in the latter case or as R14 in the former. The formyl group, after separation of the isomers, if necessary, can be reduced to $CH_3$, or can be reduced to $CH_2OH$ or converted to an oxime group, which can then be converted to a cyano group, which, in turn, can be converted to an amide. The formyl group can also be reacted with Wittig reagents to give alkyl, alkenyl or carboxy side chains or to introduce the previously identified substituents which have an amine or an alcoholic OH function in the R10 position. After the desired group has been introduced as R10, the benzochlorin or verdin can be reacted in the same way to introduce a desired group as R11. Finally, the chemistry can be used to introduce a desired group as R12. The metal complexes can be produced by the method of Example 2 or by modifications thereof which are subsequently discussed herein.

It will be appreciated that benzochlorins, verdins, porphyrin derivatives and metal complexes according to the invention where R10 through R12 are hydrogen are preferred, other factors being equal, because the production of the compounds with other groups in these positions is complicated, time consuming and expensive. The methods of Examples 8 and 9 are general in the sense that the former can be used to produce any porphyrin derivative having the structure of FIG. 9 from the corresponding purpurin while the latter can be used to produce any porphyrin derivative metal complex having the structure of FIG. 10 from the corresponding purpurin metal complex. The purpurins and purpurin metal complexes required to produce the porphyrin derivatives and porphyrin derivative metal complexes are disclosed in PCT/US86/02824.

The method of Example 2, supra, can be used to produce metal complexes of other benzochlorins, of porphyrin derivatives having the structure of FIG. 9, and of verdins. Specifically, an equivalent amount of another benzochlorin, of a porphyrin derivative, or of a verdin can be substituted for the octaethyl benzochlorin, or copper acetate, nickel acetate, cobalt acetate, silver acetate, palladium acetate, or platinum acetate can be substituted for the zinc acetate, or both substitutions can be made. In this manner, metal complexes having the formula of FIG. 1, of FIG. 2, of FIG. 5 or of FIG. 10, where M is one of the metals named above in this paragraph can be produced from the corresponding benzochlorins, verdins, or porphyrin derivatives. Other complexes can be produced by the method of Example 2 from salts containing cations other than acetate, and producing complexes which have the structures of FIGS. 1, 2 5 and 10, but where M does not represent merely a metal anion. Examples of salts that can be substituted for zinc acetate in the Example 2 procedure are identified below, together with the identity of M in FIGS. 2 and 5:

| Salt | Identity of M |
|---|---|
| $FeCl_3$ | Fe(Cl) |
| $MnCl_4$ | Mn(Cl) |
| $InCl_3$ | In(Cl) |
| $VCl_4$* | V(O) |
| $Tl(CF_3CO_2)_3$ | Tl(OAc)($H_2O$) |
| $SnCl_2$ | Sn(OH)$_2$ |
| $[Rh(CO)_2Cl]_2$ | Rh(Cl)($H_2O$) |

*Using phenol as the solvent instead of glacial acetic acid.

The procedure of Example 2 can also be modified by substituting phenol for glacial acetic acid and metal chelates of pentane, 2,4-dione for zinc acetate to produce complexes of any of the benzochlorins, verdins or porphyrin derivatives. Metals that can be so reacted (as pentane, 2,4-dione chelates) and the identity of M in the complex that is produced are set forth in the following table:

| Metal | Identity of M | Metal | Identity of M |
|---|---|---|---|
| Al | Al(acac)* | Th | Th(acac)$_2$ |
| Sc | Sc(acac) | U | U(acac)$_2$ |
| Ga | Ga(acac) | La | La(acac)$_2$ |
| In | In(acac) | Ce | Ce(acac) |
| Mo | Mo(acac) | Nd | Nd(acac) |
| Ti | Ti(acac)$_2$ | Sm | Sm(acac) |
| Zr | Zr(acac)$_2$ | Gd | Gd(acac) |
| Hf | Hf(acac)$_2$ | Tb | Tb(acac) |
| Eu | Eu(acac) | Dy | Dy(acac) |
| Pr | Pr(acac) | Ho | Ho(acac) |
| Yb | Yb(acac) | Er | Er(acac) |
| Y | Y(acac) | Tm | Tm(acac) |
| Lu | Lu(acac) | | |

*The pentane, 2,4-dione portion of a chelate thereof with a metal.

Complexes of any of the foregoing benzochlorins, verdins and porphyrin derivatives can also be produced by the procedure of Example 2, substituting dimethylformamide for glacial acetic acid and $CrCl_2$ for zinc acetate. Metal complex formation occurs at higher temperatures when dimethylformamide is used, because of its higher boiling temperature. M in the complexes is Cr(OH).

Similarly, complexes of the foregoing benzochlorins, verdins and porphyrin derivatives can be produced by the procedure of Example 2, substituting pyridine for glacial acetic acid and $PbCl_2$ for zinc acetate. M in the complexes is Pb.

The preferred metal complexes according to the invention, because optimum results have been achieved therewith, are ones where M is Zn, Sn, Al, Ag, Ce or Ga.

The production of benzochlorin, verdin and porphyrin derivative solutions in the specific non-ionic solubilizer that is available under the designation CREMOPHOR EL, and the production of emulsions of such solutions with 1,2-propanediol and saline solution is described above, as is the use of such solutions to detect and treat tumors. It will be appreciated that benzochlorins, verdins, porphyrin derivatives and their metal complexes can be dissolved in other non-ionic solubilizers and that the solutions can be used to produce emulsions that can be administrated intravenously. For example, other reaction products of ethylene oxide and castor oil can be so used, as can reaction products of ethylene, propylene and other similar oxides with other fatty acids and the reaction products of propylene and other similar oxides with castor oil. Similarly, glycols other than 1,2-propanediol can be used in producing the emulsions for intravenous administration, or the glycol can be omitted, particularly if the solubilizer is prepared to have a lower viscosity and greater compatibility with water, by comparison with the solubilizer that is available under the designation CREMOPHOR EL. It is necessary only that the solution or emulsion be one which is physiologically acceptable and of a suitable concentration, or dilutable to a suitable concentration, for intravenous administration or for local administration, should that be desirable. An indefinitely large number of such solutions and emulsions will be apparent to those skilled in the relevant art from the foregoing specific disclosure. Similarly, the aqueous phase need not be 0.9 percent w/w or any other concentration of sodium chloride. Such saline is presently favored for intravenous administration, but other aqueous phases can also be used, so long as the entire composition is physiologically acceptable for intravenous administration and, in fact, other aqueous phases may subsequently be favored. Indeed, other aqueous phases or organic phases may also be favored for local administration.

Dosages ranging of 1 mg per kg of body weight were used in the in vivo procedures described above. It has been determined only that the biological consequences described above were caused by the dosages administered, not that any dosage reported is either a minimum or a maximum. It will be appreciated, therefore, that it is necessary only to use an effective amount of a benzochlorin, verdin, porphyrin derivative or metal complex according to the invention in the detection and treatment of tumors, preferably as small a dosage as possible, and that the exact dosage can be determined by routine experimentation. While systemic administration has been described above, specifically intravenous, it will also be appreciated that local administration will be suitable, at least in some instances.

Illumination of tumors containing a benzochlorin, a verdin, a porphyrin derivative or a metal complex in accordance with the instant invention can be a surface illumination with a conventional light source, as described above, or can be a surface illumination with a laser. The illumination can also be into the body of a tumor, for example through optical fibers inserted thereinto.

Various changes and modification can be made from the specific details of the invention as described above without departing from the spirit and scope thereof as defined in the appended claims.

We claim:

1. As a composition of matter, a benzochlorin having the structure of FIG. 3 or a metal complex of a benzochlorin having the structure of FIG. 1, below,

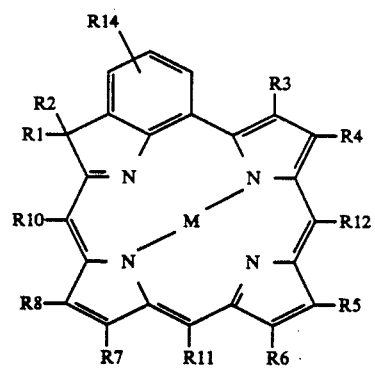

FIG. 1

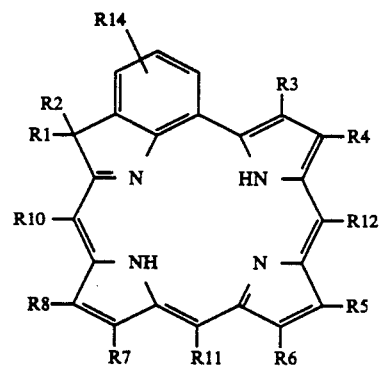

FIG. 3 wherein
M comprises a metal cation that is complexed with two of the nitrogens of the benzochlorin and is Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh, Sb, Sc, Sm, Sn, Tb, Th, Ti, Tl, Tm, U, V, Y, Yb, Zn or Zr, and
each of R1 through R8 and R10 through R12 is H or CHO,
an alkyl group other than t-butyl having from 1 to 4 carbon atoms,
an alkylene group having from 2 to 4 carbon atoms,
a group having the formula $R_2N(R_3)_2$ where $R_2$ is a bivalent aliphatic hydrocarbon radical having from 1 to 4 carbon atoms, wherein any carbon bond is either a single or a double bond, and not more than one is a double bond; $R_3$ is hydrogen or an alkyl radical having from 1 to 2 carbon atoms and the two $R_3$ groups can be the same or different,
a group having the formula $R_2N(R_4)_3 A$ where $R_2$ is a bivalent aliphatic hydrocarbon radical having from 1 to 4 carbon atoms, wherein any carbon bond is either a single or a double bond, and not more than one is a double bond; A is a physiologically acceptable anion and $R_4$ is an alkyl group having from 1 to 2 carbon atoms and the three $R_4$ groups can be the same or different,
a group having the formula $R_2OH$ were $R_2$ is a bivalent aliphatic hydrocarbon radical having from 1 to 4 carbon atoms, wherein any carbon to carbon bond is either a single or a double bond, and not more than one is a double bond, or
$CO_2R'$, $CH_2CO_2R'$ or $CH_2CH_2CO_2R'$ where R' is H, or an alkyl group other than t-butyl having from two to four carbon atoms, with the proviso that R14 can be $SO_3H$ or a salt thereof and that not more than one of R1 through R8, R10 through R12 and R14 is CHO, a group having the formula $R_2N(R_3)_2$, or a group having the formula $R_2N(R_4)_3A$.

2. As a composition of matter, a benzochlorin or a metal complex of a benzochlorin as claimed in claim 1 wherein each of R10 through R12 is hydrogen.

* * * * *

UNITED STATES PATENT AND TRADEMARK OFFICE
CERTIFICATE OF CORRECTION

PATENT NO. : 4,988,808
DATED : Jan. 29, 1991
INVENTOR(S) : Alan R. Morgan, Steven H. Selman It is certified that error appears in the above-identified patent and that said Letters Patent is hereby corrected as shown below:

column 16, line 37 should read

—each of R1 through R8, [and] R10 through R12 and R14 is H or— column 16, line 69

3. As a composition of matter, a benzochlorin or a metal complex of a benzochlorin as claimed in claim 2 wherein each of R1 through R8 is methyl or ethyl.

4. As a composition of matter, a benzochlorin or a metal complex of a benzochlorin as claimed in claim 3 wherein R1, R3, R5 and R7 are the same and R2, R4, R6 and R8 are the same, but are different from R1, R3, R5 and R7.

5. As a composition of matter, a benzochlorin as claimed in claim 4.

6. As a composition of matter, a metal complex of a benzochlorin as claimed in claim 4.

7. As a composition of matter, a metal complex of a benzochlorin as claimed in claim 6 wherein M is Zn, Sn, Al, Ag, Ce or Ga.

8. As a composition of matter, a benzochlorin or a metal complex of a benzochlorin as claimed in claim 4 wherein R1, R3, R5 and R7 are methyl, and R2, R4, R6 and R8 ethyl.

9. As a composition of matter, a benzochlorin as claimed in claim 8.

10. As a composition of matter, a metal complex of a benzochlorin as claimed in claim 8.

11. As a composition of matter, a metal complex of a benzochlorin as claimed in claim 10 wherein M is Zn, Sn, Al, Ag, Ce or Ga.

UNITED STATES PATENT AND TRADEMARK OFFICE
CERTIFICATE OF CORRECTION

PATENT NO. : 4,988,808

DATED : Jan. 29, 1991

INVENTOR(S) : Alan R. Morgan, Steven H. Selman

It is certified that error appears in the above-identified patent and that said Letters Patent is hereby corrected as shown below:

12. As a composition of matter, a benzochlorin or a metal complex of a benzochlorin as claimed in claim 2 wherein each of R1 through R8, is ethyl.

13. As a composition of matter, a benzochlorin as claimed in claim 12.

14. As a composition of matter, a metal complex of a benzochlorin as claimed in claim 12.

15. As a composition of matter, a metal complex of a benzochlorin as claimed in claim 14 wherein M is Zn, Sn, Al, Ag, Ce or Ga.

16. As a composition of matter, a benzochlorin or a metal complex of a benzochlorin as claimed in claim 28 wherein R1, R3, R5 and R7 are ethyl, and R2, R4, R6 and R8 methyl.

17. As a composition of matter, a benzochlorin as claimed in claim 16.

18. As a composition of matter, a metal complex of a benzochlorin as claimed in claim 16.

19. As a composition of matter, a metal complex of a benzochlorin as claimed in claim

UNITED STATES PATENT AND TRADEMARK OFFICE
CERTIFICATE OF CORRECTION

PATENT NO. : 4,988,808

DATED : January 29, 1991

INVENTOR(S) : Alan R. Morgan, et. al.

It is certified that error appears in the above-identified patent and that said Letters Patent is hereby corrected as shown below:

18 wherein M is Zn, Sn, Al, Ag, Ce or Ga.

Signed and Sealed this

Eighteenth Day of August, 1992

*Attest:*

DOUGLAS B. COMER

*Attesting Officer*     *Acting Commissioner of Patents and Trademarks*